United States Patent [19]

Jacobs et al.

[11] Patent Number: 4,616,089

[45] Date of Patent: Oct. 7, 1986

[54] SYNTHETIC ANTI-INFLAMMATORY DERIVATIVES OF MANOALIDE

[75] Inventors: Robert S. Jacobs, Santa Barbara; D. John Faulkner, La Jolla, both of Calif.

[73] Assignee: University of California, Berkeley, Calif.

[21] Appl. No.: 621,879

[22] Filed: Jun. 18, 1984

Related U.S. Application Data

[63] Continuation-in-part of Ser. No. 519,853, Aug. 3, 1983, abandoned.

[51] Int. Cl.[4] .......................................... C07D 307/58
[52] U.S. Cl. .................................. 549/323; 549/294; 549/318; 514/461
[58] Field of Search ........................................ 549/323

[56] References Cited

U.S. PATENT DOCUMENTS 4,447,445  5/1984  Jacobs et al. ........................ 514/460

*Primary Examiner*—Norma S. Milestone
*Attorney, Agent, or Firm*—Ciotti & Murashige

[57] ABSTRACT

Synthetic analogs of the marine natural product manoalide include 3,7-Bis(hydroxymethyl)-4-hydroxy-11-methyl-13-(2',6',6'-trimethylcyclohexenyl)-2,6,10-tridecatrienoic acid γ-lactone, manoalide δ-lactone, manoalide δ-lactone acetate and dehydro-seco-manoalide.

The method of treating mammals including humans in need of a drug having analgesic and/or anti-inflammatory activity comprising the administration of a therapeutically effective amount of a synthetic analog of manoalide.

1 Claim, No Drawings

SYNTHETIC ANTI-INFLAMMATORY DERIVATIVES OF MANOALIDE

This invention was made with Government support under Sea Grant No. NA 80 AA-D-00120, Project No. R/MP-21, awarded by the National Oceanic and Atmospheric Administration. The Government has certain rights in this invention.

This application is a continuation-in-part of application Ser. No. 519,853, filed Aug. 3, 1983, now abandoned.

BACKGROUND OF THE INVENTION

Concurrently filed U.S. patent application Ser. No. 519,852, now U.S. Pat. No. 4,447,445 relates to the discovery of the analgesic and anti-inflammatory properties of manoalide.

The present invention relates to synthetic analogs of manoalide which have been shown to have anti-inflammatory activity in the same range as that of manoalide, i.e., greater than that of indomethacin and less than that of hydrocortisone. Potential uses include treatment of rheumatoid arthritis, osteoarthritis, rheumatic carditis, collagen and/or auto-immune diseases such as myasthenia gravis, allergic diseases, bronchial asthma and ocular and skin inflammatory diseases. These drugs are also likely to be useful as adjuvant therapy associated with organ and tissue transplants and as a local treatment for any venom in which a major constituent is the enzyme phospholipase $A_2$. Since manoalide blocks oxazolone induced inflammation this compound would be useful in treating forms of allergic contact dermatitis (such as poison oak or poison ivy).

For these reasons, it is believed that the present invention makes a further and significant contribution to the pharmaceutical arts.

SUMMARY OF THE INVENTION

Briefly, the present invention comprises synthetic analogs of the marine natural product manoalide including 3,7-Bis(hydroxymethyl)-4-hydroxy-11-methyl-13-(2',6',6'-trimethylcyclohexenyl)-2,6,10-tridecatrienoic acid γ-lactone, manoalide δ-lactone, manoalide δ-lactone acetate and dehydro-seco-manoalide.

Manoalide has the following structural formula:

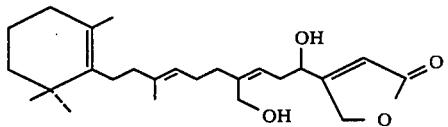

The method of treating mammals including humans in need of a drug having analgesic and/or anti-inflammatory activity comprising the administration of a therapeutically effective amount of a synthetic analog of manoalide.

It is an object of this invention to provide new synthetic analogs of manoalide.

It is also an object of this invention to provide a novel therapeutic method employing synthetic analogs of manoalide.

These and other objects and advantages of this invention will be apparent from the detailed description which follows.

Synthetic analogs of manoalide are administered to mammals including humans according to this invention in an effective amount of 10 to 50 milligrams per day per kilogram of body weight. The drugs may be administered orally, parenterally or by other standard administration routes. The dosage form may be by tablet containing normal acceptable additives, excipients, etc. The parenteral form contains typical aqueous intravenous solution ingredients.

DESCRIPTION OF THE PREFERRED EMBODIMENTS

The following Examples are presented solely to illustrate the invention and are not limiting in any way. In the Examples the parts and percentages are by weight unless otherwise indicated.

EXAMPLE I

Preparation of 3,7-Bis(hydroxymethyl)-4-hydroxy-11-methyl-13-(2',6',6'-trimethylcyclohexenyl)-2,6,10-tridecatrienoic acid γ-lactone Excess sodium borohydride (300 mg, 7.0 mmole) was added in small portions to a stirred solution of manoalide (136 mg, 0.33 mmole) in isopropanol (20 mL) at 0° C. The mixture was stirred at 0° C. for one hour. Excess reagent was destroyed by dropwise addition of 2% hydrochloric acid until hydrogen evolution ceased. The product was partitioned between water (100 mL) and ether (2×100 mL), the ether extract dried over sodium sulfate and then solvent removed to obtain an oil. The product was purified by HPLC to obtain the diol. Yield 75 mg (55% theoretical); oil;* $^1$H NMR (CDCl$_3$) δ0.99 (s, 6H), 1.60 (s, 3H), 1.65 (s, 3H), 4.11 (d, 1H, J=14 HZ), 4.17 (d, 1H, J=14 Hz), 5.39 (t, 1H, J=7 Hz), 5.98 (br s, 1H); HRMS. m/z 402.2770, C$_{25}$H$_{38}$O$_4$ requires 402.2770.

*IR(film) 3350, 1775 cm$^{-1}$

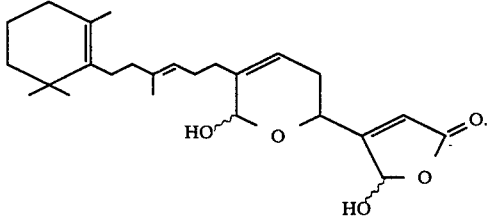

EXAMPLE II

Preparation of manoalide δ-lactone

A solution of Jones' reagent [prepared from chromium trioxide (6.7 g) and sulfuric acid (6 mL)] was added dropwise to a stirred solution of manoalide (30 mg, 0.07 mmole) in distilled acetone (20 mL) at 25° C. until the solution remained brown. After five minutes, the reaction mixture was filtered through a short column of silica gel and the solvent evaporated to obtain an oil. The product was chromatographed by HPLC to obtain the manoalide δ-lactone as a mixture of two diastereoisomers. Yield 15 mg (50% theoretical); oil;* $^1$H NMR (CDCl$_3$) δ0.99 (s, 6H), 1.60 (s, 3H), 1.65 (s, 3H), 5.10 (m, 1H), 5.26 (dd, 0.5H, J=12, 5 Hz), 5.37 (dd, 0.5H, J=12, 5 Hz), 6.15 (s, 0.5H), 6.20 (d, 0.5H, J=7 Hz), 6.23 (s, 0.5H), 6.35 (d, 0.5H, J=7 Hz), 6.62 (m, 0.5H), 6.65 (m, 0.5H); HRMS. m/z 414.2384, $C_{25}H_{34}O_5$ requires 414.2406.
*IR(film) 3300, 1770, 1740 cm$^{-1}$; UV(MeOH) 208.5 nm ($\epsilon$10,350)

Manoalide δ-lactone is an inseparable 1:1 mixture of diasteroisomers resulting from epimerization at the hemiacetal carbon atom.

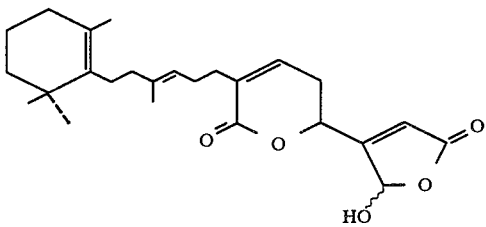

EXAMPLE III

Preparation of manoalide δ-lactone acetate

Manoalide δ-lactone (15 mg, 0.04 mmole) was dissolved in acetic anhydride (0.5 mL) and pyridine (1.0 mL) and the mixture was stirred at 25° C. for four hours. The solvents were removed under high vacuum and the residue dissolved in ether and filtered through a silica gel plug to obtain a clear oil. The oil was chromatographed by HPLC to obtain a mixture of diasteroisomeric acetates. Yield 16 mg (quantitative; oil;* $^1$H NMR (CDCl$_3$) δ0.99 (s, 3H), 1.59 (s, 3H), 1.65 (s, 3H), 2.18 (s, 3H), 5.10 (t, 1H, J=7 Hz), 5.21 (m, 1H), 6.26 (s, 0.4H), 6.34 (s, 0.6H), 6.61 (m, 1H), 6.98 (s, 1H), HRMS. m/z 456.2514, $C_{27}H_{36}O_6$ requires 456.2512.
*IR(film) 1800, 1770, 1725 cm$^{-1}$; UV(MeOH) 208 nm ($\epsilon$10,600)

Manoalide δ-lactone acetate is a 6:4 mixture of two diastereoisomers. The diastereoisomers can be separated but the material assayed was the mixture of isomers.

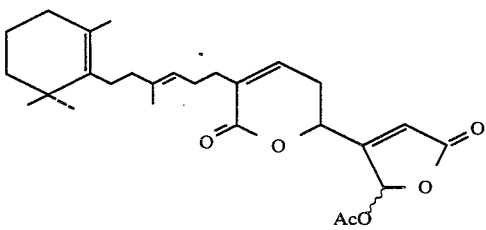

EXAMPLE IV

Mouse Ear Anti-inflammatory Assay

Test compound and phorbol myristate acetate (PMA) are topically applied simultaneously to the left ears of mice. Three hours, 20 minutes after application, the mice are sacrificed, left and right ears removed and standard sized bores taken. Edema (inflammation) is measured as the difference in weight between left and right ears [Van Arman, C. G., Clin. Pharmacol. Ther. 16:900–904 (1974)].

TABLE I

| INHIBITION OF PMA-INDUCED INFLAMMATION** BY MANOALIDE AND MANOALIDE DERIVATIVES | | |
|---|---|---|
| COMPOUND | DOSE (ug/ear) | AVERAGE EAR WEIGHT (mg/ear) |
| MANOALIDE | 7.5 | 20.45 |
|  | 10.0 | 19.75 |
|  | 20.0 | 17.00* |

TABLE I-continued

| INHIBITION OF PMA-INDUCED INFLAMMATION** BY MANOALIDE AND MANOALIDE DERIVATIVES | | |
|---|---|---|
| COMPOUND | DOSE (ug/ear) | AVERAGE EAR WEIGHT (mg/ear) |
|  | 40.0 | 16.80* |
|  | 80.0 | 12.90* |
|  | 160.0 | 12.60* |
|  | 320.0 | 11.20* |
| MANOALIDE DIOL | 25.0 | 14.54* |
|  | 50.0 | 13.17* |
| MANOALIDE δ LACTONE | 25.0 | 16.38* |
|  | 50.0 | 14.87* |
| MANOALIDE δ LACTONE ACETATE | 25.0 | 16.64* |
|  | 50.0 | 13.34* |

*STATISTICALLY SIGNIFICANT DIFFERENCE, STUDENT'S T-TEST, $P \leq .05$
**PMA DOSE = 1.5 ug/ear Results As shown in Table I, the level of activity of all three compounds is approximately equivalent to that of manoalide when tested for the ability to inhibit PMA-induced inflammation in the mouse ear. For purposes of comparison, the average weight of an untreated mouse ear is 9.3 mg (100% inhibition) and the average weight of an ear treated with PMA alone is 23 mg (0% inhibition). Manoalide acetate was compared with manoalide in a separate study using a higher concentration of PMA and was also found to be active (Table II).

TABLE II

| INHIBITION OF PMA-INDUCED INFLAMMTION** BY MANOALIDE AND MANOALIDE DERIVATIVES | | |
|---|---|---|
| COMPOUND | DOSE (ug/ear) | AVERAGE EAR WEIGHT (mg/ear) |
| MANOALIDE | 300.0 | 17.46* |
| MANOALIDE ACETATE | 300.0 | 19.01* |
|  | 150.0 | 21.53 |

*STATISTICALLY SIGNIFICANT DIFFERENCE, STUDENT'S T-TEST, P = .05
**PMA DOSE = 5.0 ug/ear

EXAMPLE V

Isolation and Characterization of dehydro-seco-manoalide

Examination of UV and $^1$H NMR data of the crude extracts of the sponge Luffariella variabilis provided evidence that dehydro-seco-manoalide was not a natural product but was formed during chromatography, presumably by acid-catalyzed dehydration of manoalide on silica.

The isolation and purification of manoalide requires two or three chromatographic separations on silica gel. Fractions that eluted before manoalide were saved and certain fractions, distinguished by their $^1$H NMR spectra, combined. The combined fractions were chromatographed by LC on μ-Porasil using diethyl ether as eluant to obtain dehydromanoalide as a viscous yellow oil. As is typical of an artifact of isolation, the yield is variable.

Dehydro-seco-manoalide

UV (EtOH) 316 nm ($\epsilon$12000), 205 nm ($\epsilon$10300) UV (EtOH+NaOH) 461 nm ($\epsilon$25000), 280 nm ($\epsilon$1600), 246 ($\epsilon$2000) IR (CHCl$_3$) 1745 cm$^{-1}$, 1670 cm$^{-1}$ $^1$H NMR (CDCl$_3$) δ0.96 (s, 6H), 1.56 (s, 3H), 1.60 (s, 3H), 5.11 (br t, 1H, J=7 Hz), 6.14 (s, 1H), 6.32 (s, 1H), 6.82 (d, 1H, J=15.5 Hz), 6.91 (d, 1H, J=6 Hz), 7.34 (dd, 1H, J=15.5, 6 Hz), 9.52 (s, 1H). $^{13}$C NMR (CDCl$_3$) δ194.3 (d), 171.5 (s), 160.0 (d), 146.3 (s), 145.8 (d), 137.8 (s), 136.8 (s), 133.8 (s), 128.3 (d), 126.9 (s), 121.8 (d), 119.5 (d), 97.8 (d), 40.1 (t), 39.7 (t), 34.8 (s), 32.6 (t), 29.5 (t), 28.5 (q), 28.5 (q), 27.7 (t), 24.6 (t), 19.7 (q), 19.4 (t), 16.0 (q). Mass spectrum, m/z (%), 398 (3), 380 (3), 251 (6), 137 (100). Mass measurement, m/z=398.2429, C$_{25}$H$_{34}$O$_4$ requires 398.2457.

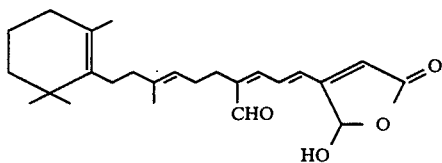

TABLE III

Effect of dehydro-seco-manoalide on phorbol-induced inflammation in the mouse ear (Phorbol myristate acetate, 1.5 ug/ear.)

| Agent | Dose ug/ear | N | Mg. Ear Weight + S.E. |
|---|---|---|---|
| None | — | 13 | 24.60 ± 0.88 |
| Dehydro-seco-manoalide | 50 | 8 | 14.13 ± 0.79* |
| Relative Potency | | | |

Equivalent does response to manoalide = 66 ug/ear.
Equivalent does dehydro-seco-manoalide = 50 ug/ear.
Relative Potency = 1.32

*Statistically significant decrease (p < 0.01) relative to phorbol myristate acetate alone, Student's t-test.

TABLE IV

Effect of manoalide and dehydro-seco-manoalide on purified bee venom phospholipase A$_2$

| | PERCENT INHIBITION OF CONTROL | |
|---|---|---|
| CONC μM | MANOALIDE | DEHYDRO-SECO-MANOALIDE |
| 0.25 | 20.7 | 30.3 |
| 0.50 | 48.0 | 61.8 |
| 0.75 | 73.5 | 51.3 |
| 2.00 | 92.8 | 72.4 |
| 4.00 | 94.5 | 87.3 |

Measurment of phospholipase A$_2$ activity by Radiometer pH stat. Standard assay conditions: pH 7.4, 41° C., 1.36 mM phosphatidylcholine dipalmitoyl, 2.76 mM Triton X-100, and 1.0 mM Ca$^{+2}$.

Having fully described the invention, it is intended that it be limited only by the lawful scope of the appended claims.

We claim:

1. 3,7-Bis(hydroxymethyl)-4-hydroxy-11-methyl-13-(2',6',6'-trimethylcyclohexenyl)-2,6,10-tridecatrienoic acid γ-lactone.

* * * * *